(12) United States Patent
Pasquini et al.

(10) Patent No.: US 7,091,395 B2
(45) Date of Patent: Aug. 15, 2006

(54) ANTISEPTIC TAMPON AND METHOD OF PREPARING IT

(75) Inventors: Jean-Bastien Pasquini, 93 rue de la Gare, 3335 Leudelange (LU); Michel Pasquini, Carsac-Aillac (FR)

(73) Assignee: Jean-Bastien Pasquini, Leudelange (LU)

( * ) Notice: Subject to any disclaimer, the term of this patent is extended or adjusted under 35 U.S.C. 154(b) by 372 days.

(21) Appl. No.: 10/470,569

(22) Filed: Jun. 2, 2003

(65) Prior Publication Data

US 2005/0070865 A1 Mar. 31, 2005

Related U.S. Application Data

(60) Division of application No. 10/173,098, filed on Jun. 18, 2002, which is a continuation of application No. PCT/FR00/03681, filed on Dec. 26, 2000.

(30) Foreign Application Priority Data

Dec. 29, 1999 (FR) .................................. 99 16847

(51) Int. Cl.
*A61F 13/20* (2006.01)

(52) U.S. Cl. ....................... 604/360; 604/363; 604/904; 28/118

(58) Field of Classification Search ................. 604/360, 604/363, 385.18, 904, 15; 28/118
See application file for complete search history.

(56) References Cited

U.S. PATENT DOCUMENTS

| | | | |
|---|---|---|---|
| 3,058,469 A * | 10/1962 | Crockford | 604/363 |
| 3,139,886 A * | 7/1964 | Tallman et al. | 604/12 |
| 3,756,238 A | 9/1973 | Hanke | |
| 3,918,452 A * | 11/1975 | Cornfeld | 604/515 |
| 4,312,348 A * | 1/1982 | Friese | 604/363 |
| 4,428,747 A * | 1/1984 | Friese et al. | 604/12 |
| 4,582,717 A * | 4/1986 | von Bittera et al. | 427/2.31 |
| 4,648,513 A * | 3/1987 | Newman | 383/204 |
| 4,983,163 A * | 1/1991 | Winans et al. | 604/522 |
| 5,133,457 A * | 7/1992 | Kadel | 206/438 |
| 5,417,224 A | 5/1995 | Petrus et al. | |
| 5,529,782 A * | 6/1996 | Staab | 424/436 |
| 5,679,369 A * | 10/1997 | Brown-Skrobot | 424/431 |
| 6,746,418 B1* | 6/2004 | Pauley et al. | 604/12 |

FOREIGN PATENT DOCUMENTS

| | | |
|---|---|---|
| DE | 2309575 | 9/1974 |
| EP | 0110793 | 3/1987 |
| WO | WO 92/13577 * | 8/1992 |
| WO | WO 9213577 A1 * | 8/1992 |
| WO | WO 0037118 A | 6/2000 |

* cited by examiner

*Primary Examiner*—Tatyana Zalukaeva
*Assistant Examiner*—C. Lynne Anderson
(74) *Attorney, Agent, or Firm*—Lawrence E. Laubscher, Sr.; Lawrence E. Laubscher, Jr.

(57) ABSTRACT

The invention relates to an antiseptic tampon and a method of preparing it, which method consists of introducing metered quantities of a liquid mixture of antiseptic product and hydrophobic excipient into individual sheaths (14) for packaging tampons, then introducing standard tampons (22) into said sheaths (14) so that their lower ends are immersed in the mixture of antiseptic product and excipient, and then closing and sealing said sheaths (14).

3 Claims, 1 Drawing Sheet

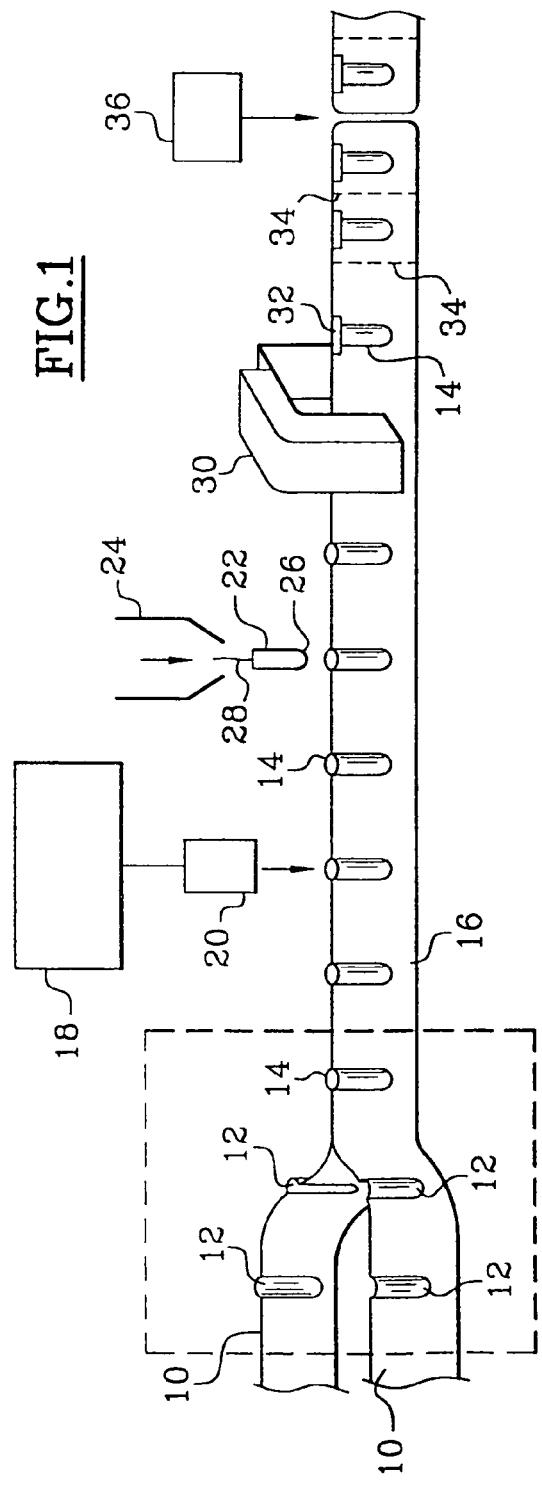
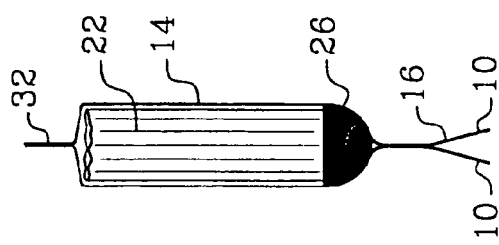

ANTISEPTIC TAMPON AND METHOD OF PREPARING IT

REFERENCE TO RELATED APPLICATION

This application is a division of application Ser. No. 10/173,098 filed Jun. 18, 2002, which in turn is a continuation of the PCT International Application No. PCT/FR00/03681 filed Dec. 26, 2000, which is based on the French Application No. 99-16847 filed Dec. 29, 1999.

BACKGROUND OF THE INVENTION

1. Field of the Invention

The invention relates to an antiseptic tampon and a method of preparing it.

2. Description of the Prior Art

A standard tampon is known to constitute a focus of potential infection of the vagina because its insertion can be accompanied by the introduction of more or less pathogenic bacteria present in the vulva and on the surrounding skin surface. The tampon is made from an absorbent material and tends to dry the mucous membranes of the vagina, which makes them fragile and more sensitive to various infections.

To reduce this inconvenience it has been proposed to make tampons from a less absorbent material, although they then have to be changed more frequently, for example every four hours, which is highly inconvenient and a great nuisance.

A tampon has also been proposed, in particular in the document EP-A-0 110 793, which has a cup-shaped cell at one end and a pessary containing an antiseptic or medication and fixed into the cell by a soluble adhesive gum. When the tampon is inserted, the pessary is in the vicinity of the neck of the uterus and renders aseptic the vagina and the blood flowing into the vagina.

The above tampon is difficult to mass produce economically, in particular because of the cell formed at the end of the tampon, the application of a soluble adhesive gum and the placing of a pessary of antiseptic or medication in the cell.

OBJECTS OF THE INVENTION

The object aims particularly to provide a simple, effective and economic solution to the problems cited above.

An object of this invention is an aseptic tampon which avoids the risks of infection of the vagina without making the mucous membranes of the vagina fragile.

Also an object of this invention is an antiseptic tampon which is prepared from a standard tampon.

A further object of this invention is a method of preparing an antiseptic tampon which is economical and which lends itself to automatic mass production on machines of a type known in the art.

SUMMARY OF THE INVENTION

Accordingly, the invention proposes a method of preparing a tampon made from an absorbent material and containing an antiseptic product, characterized in that it consists of introducing metered quantities of a liquid mixture of antiseptic product and hydrophobic excipient into individual tampon packaging sheaths, then introducing tampons into said sheaths so that their ends intended to be covered with said mixture are at the bottom of said sheaths and in contact with the mixture, and closing and sealing said sheaths.

Thus tampons in accordance with the invention are prepared concomitantly with packaging them, in a particularly simple and economic manner.

According to another further characteristic of the invention, this method also consists of preparing the mixture of antiseptic product and excipient by heating the excipient to melt it, adding the antiseptic product to the molten excipient and mixing the antiseptic product and the excipient before pouring the mixture into the packaging sheaths, and then solidifying the mixture of antiseptic product and excipient on the tampons by cooling after closing the sheaths.

This produces a lubricating, hydrophobic, antiseptic and strong covering of the end of the tampon which is inserted into the vagina first.

Advantageously, the method according to the invention also consists of thermoforming semicylindrical cells in two strips of plastics material, for example PVC, the cells opening onto a lateral edge of said strips, applying the two strips face-to-face to form said sheaths by joining two facing cells, and heat-welding the two strips together.

A method of the above kind can be executed on machines of a type known in the art, used in particular to manufacture suppositories, and therefore requires a small investment in hardware, since it is sufficient to adapt existing machines.

According to another feature of the invention, Döderlein's bacillus (*lactobacillus casei*) is added to the mixture of the excipient and the antiseptic product before they are poured into the packaging of the tampons, for example in freeze-dried form and at a rate of the order of 90 mg per tampon.

The tampons prepared in the above way are intended to be used at the end of a menstrual period, to reseed the flora normally present in the vagina.

The invention also proposes an antiseptic tampon, prepared by the method above-described, characterized in that the mixture of the antiseptic product and the hydrophobic excipient forms a covering of an end portion of the tampon.

This mixture of antiseptic product and hydrophobic excipient covers the end part of the tampon in the vicinity of the neck of the uterus when the tampon is in place and prevents all risk of drying the mucous membranes of the vagina or making them fragile, with an additional antiseptic effect which protects the vagina from the risks of infection.

The hydrophobic excipient is advantageously a lubricant which facilitates inserting the tampon and avoids the need to use an applicator.

In a preferred embodiment of the invention, the antiseptic product is nonoxynol 9.

The above product has been used for more than thirty years as a spermicide in many preparations for vaginal application and its good local and general tolerance have been proven by many studies.

According to another feature of the invention, this antiseptic tampon is prepared from a standard tampon.

This feature greatly reduces the unit cost of the tampon according to the invention.

BRIEF DESCRIPTION OF THE DRAWINGS

The invention will be better understood and other features, details and advantages of the invention will become more clearly apparent after reading the following description, which is given by way of example and with reference to the accompanying drawings, in which:

FIG. 1 is a diagram showing essential steps of a method according to the invention;

FIG. 2 is a diagrammatic view of a tampon in accordance with the invention inside its individual packaging.

DESCRIPTION OF THE PREFERRED EMBODIMENTS

In the method shown in FIG. 1, the first step consists of paying out two strips 10 of a heat-sealable plastics material, such as polyvinyl chloride, for example, and thermoforming semicylindrical cells 12 in each of the strips, the cells opening at one end onto a lateral edge of the corresponding strip 10, whereas their other end is at a distance from the other lateral edge of the strip 10.

The two strips 10 are then moved towards each other and pressed together with their semicylindrical cells substantially vertical and facing each other to form cylindrical sheaths 14 open at the top.

The two strips 10 are fixed together to form a single strip except in a lateral area 16 in which the two strips 10 remain separate from each other, this lateral area 16 extending along the lateral edge of the strips 10 on the same side as the bottoms of the sheaths 14.

In a preferred embodiment of the invention, the two strips 10 are heat-welded together at a temperature of approximately 200° C.

The next step of the method consists of pouring into each sheath 14 a metered quantity of a liquid mixture containing an antiseptic product and a hydrophobic and lubricating excipient.

The mixture is prepared by melting the excipient, which is advantageously based on glycerides, for example the product SUPPOCIRE AM sold by GATTEFOSSE. The product is placed in a tank 18 with thermostatically controlled heating walls. This tank is heated to a temperature of approximately 50–55° C., for example, and a quantity of excipient is then placed in it, for example approximately 60 kg; the excipient is then maintained in the molten state in the tank at a temperature in the order of 38° C. The tank 18 is equipped with a paddle-blade stirrer for mixing the excipient in the tank until it has all melted.

A predetermined quantity of an antiseptic product is then added to the tank, preferably nonoxynol 9, which is an anhydrous viscous liquid, principally composed of polyethylene glycol monononylphenyl ethers, with the general formula $C_9H_{19}C_6H_4$—$(OCH_2$—$CH_2)_n$—$OH$, where n is generally equal to 9 but can be from 6 to 16.

5 kg of nonoxynol 9 and 65 kg of excipient are placed in the tank 18, for example, and mixed for approximately 30 minutes at 38° C. to obtain a homogeneous mixture.

The tank 18 is connected to metering apparatus 20 of a type known in the art for pouring the mixture of antiseptic product and excipient into the sheaths 14, at a rate of 700 mg per sheath, for example, to fill the lower ends of the sheaths.

Standard tampons 22 are then inserted into the sheaths 14, for example manually or by means of an automatic feed system 24, so that the rounded end 26 of the tampon is immersed in the mixture contained in the bottom of the sheath 14.

The standard tampon 22 is made from natural fibers (viscose and/or cotton) contained in a soft web of a non-woven textile material and possibly includes an extraction cord 28 made from a hydrophobic material.

The sheaths 14 containing the tampons 22 then move to a sealing and marking station 30 in which the upper end 32 of each sheath 14 is sealed and printed with a batch number and an expiry date.

The sheaths 14 then enter a tunnel in which they are cooled to room temperature, at which the mixture of antiseptic product and excipient covering the lower end portion of each tampon 22 solidifies.

Pre-cut transverse lines 24 are formed in the strips 10 between the sheaths 14.

Cutting means 36 then cut the strips 10 into cards containing a predetermined number of tampons packaged in the sheaths 14. The cards can themselves be packaged in cardboard cartons on which the corresponding batch numbers and expiry dates are printed.

FIG. 2 is a diagram showing to a larger scale a tampon according to the invention in its individual packaging sheath 14.

The lower end 26 of the tampon 22 has a solid covering consisting of the mixture of the antiseptic product and the hydrophobic and lubricating excipient and the lower end of the sheath 14 is extended by two independent flaps formed by the parts of the strips 10 in the free area 16 between two transverse cuts 34, enabling the sheath to be opened easily by pulling on these two flaps.

The quantity of antiseptic product that each tampon includes can obviously be varied to some degree. It is less than approximately 150 mg and preferably of the order of 50 mg in the case of nonoxynol 9. Similarly, the quantity of hydrophobic and lubricating excipient can vary about the value of 650 mg per tampon, for example from approximately 500 to 800 mg.

The preparation of tampons in accordance with the invention, which uses standard tampons and existing machines for manufacturing suppositories, is highly economical and requires a relatively small investment.

The antiseptic product and the hydrophobic and lubricating excipient used are very well tolerated and have virtually no contra-indications, with the result that the tampon according to the invention does not cause any irritation of the mucous membranes of the vagina, and tests have shown that it can be classified as a material that is not sensitized by contact with the skin.

Repeated use of the tampon reduces and prevents the risks of infection and strengthens the protection of the mucous membranes of the vagina.

The tampon according to the invention can also be used at the end of a menstrual period to reseed the flora normally present in the vagina. To this end, Döderlein's bacillus (*Bacillus casei*) is added to the mixture of the antiseptic product and the excipient poured into the packaging sheaths 14. Döderlein's bacillus is available in freeze-dried form and is metered at a rate of the order of 80 to 120 mg per tampon, preferably approximately 90 mg.

The invention claimed is:

1. A method of preparing a tampon made from an absorbent material and containing an antiseptic product, comprising:

(a) heating an hydrophobic excipient to melt it;
   (b) adding an antiseptic product with the melted excipient to form a liquid mixture;
   (c) pouring a metered quantity of the liquid mixture into a vertically arranged individual tampon packaging sheath, whereby the liquid mixture is contained in the bottom of the sheath;
   (d) introducing a tampon downwardly into the sheath so that one end of the tampon is immersed in said mixture at the bottom of the sheath;
   (e) closing and sealing the sheath; and
   (f) solidifying the mixture on the tampon by cooling.

2. A method according to claim 1, and further including adding Döderlein's bacillus to the liquid mixture of the antiseptic product and excipient before pouring the mixture into the sheath.

3. A method according to claim 1, and further including thermoforming semi-cylindrical cells in two strips of plastics material, the cells opening onto a lateral edge of said strips, applying the two strips face-to-face to form said sheath by joining two facing cells, and heat-welding the two strips together.

* * * * *